(12) United States Patent
Sugito

(10) Patent No.: US 7,449,016 B2
(45) Date of Patent: Nov. 11, 2008

(54) DISPOSABLE WEARING ARTICLE

(75) Inventor: Tomoko Sugito, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 0 days.

(21) Appl. No.: 11/249,379

(22) Filed: Oct. 14, 2005

(65) Prior Publication Data

US 2006/0084936 A1     Apr. 20, 2006

(30) Foreign Application Priority Data

Oct. 15, 2004     (JP) ................... 2004-301262

(51) Int. Cl.
*A61F 13/15*     (2006.01)
*A61F 13/20*     (2006.01)

(52) U.S. Cl. ................ 604/385.26; 604/385.01; 604/396

(58) Field of Classification Search . 604/385.24–385.3, 604/385.01, 386–387, 396
See application file for complete search history.

(56) References Cited

U.S. PATENT DOCUMENTS

| | | | | |
|---|---|---|---|---|
| 6,149,639 A | * | 11/2000 | Lundberg et al. | ........... 604/386 |
| 2003/0735190 | | 7/2003 | Widlunc et al. | |
| 2004/0006327 A1 | | 1/2004 | Karami | |
| 2004/0236303 A1 | | 11/2004 | Igaue et al. | |
| 2005/0177126 A1 | | 8/2005 | Kurata | |

FOREIGN PATENT DOCUMENTS

| | | |
|---|---|---|
| EP | 1166736 | 1/2002 |
| GB | 2267024 | 11/1993 |
| JP | 3059224 U | 3/1999 |
| JP | 3096152 | 8/2000 |
| WO | 9530397 | 11/1995 |
| WO | 9723180 | 7/1997 |
| WO | 9736566 | 10/1997 |
| WO | WO 00/37010 | 6/2000 |
| WO | WO 01/13843 | 3/2001 |
| WO | WO 01/13845 | 3/2001 |

* cited by examiner

*Primary Examiner*—Michele Kidwell
(74) *Attorney, Agent, or Firm*—Lowe, Hauptman, Ham & Berner, LLP

(57) ABSTRACT

A wearing article includes a pair of connector sheet strips extending inward from transversely opposite side edges of the wearing article and serving to connect front and rear waist regions. The connector sheet strips can be easily turned around so as to extend outward from the side edges. Each of the connector sheet strips includes a proximal end overlapped and bonded together with an inner surface of a lateral margin of the wearing article and a deformable flap portion extending inward from the proximal end in a transverse direction of the wearing article and provided with a fastener element. The proximal end bows together with the lateral margin so that the proximal end lies on the convex side and the lateral margin lies on the concave side.

17 Claims, 6 Drawing Sheets

DISPOSABLE WEARING ARTICLE

BACKGROUND OF THE INVENTION

The present invention relates to a disposable wearing article suitable for use in various forms such as a disposable diaper, a disposable diaper for incontinent patient, a disposable diaper cover and disposable training pants.

Disposable diapers having front and rear waist regions adapted to be detachably connected with each other by sheet-like fasteners are well known. In one example of such a well known disposable diaper, each of the fasteners has its one end as viewed in a transverse direction of the diaper is permanently bonded to one of front and rear waist regions in the vicinity of the associated one of transversely opposite side edges. The disposable diaper 100 of this type shown in FIGS. 5 and 6 is disclosed, for example, in Japanese Patent No. 3096152 (REFERENCE). The diaper 100 has a pair of connector sheet strips as fasteners. Transversely opposite side edges 103, 103 of the front waist region 101 and transversely opposite side edges 104, 104 of the rear waist region 102 are put flat together, then proximal ends 107, 107 of the respective connector sheet strips 106, 106 having distal ends provided on inner surfaces with engagement members 105 are put flat together with the transversely opposite side edges 103, 103 of the front waist region 101. These portions put flat together are bonded together to define joint zones 108. Immediately inside these joint zones 108, the front waist region 101 is formed with cutting lines 109*a*, 109*a* along which the front waist region 101 is cut off from the rear waist region 102. In other words, this diaper 100 initially has the pants-type and may be put on the wearer's body without any modification when it is desired to put the diaper 100 on the wearer standing up. In this case, the connector sheet strips 106 are not used and locked on the front waist region 101 by means of the engagement members 105 without an anxiety that these connector sheet strips 106 might unintentionally move during use of the diaper 100. When it is desired to put the diaper 100 on the wearer lying down, the front waist region 101 or the connector sheet strips 106 may be pulled so as to tear the front waist region 101 off from the rear waist region 102 along the cutting lines 109*a* and thereby to convert the diaper 101 from the initial pants-type to the open-type as shown in FIG. 6. After putting the diaper on the wearer, the connector sheet strips 106 may be anchored on the front waist region 101 at appropriate positions.

In the case of the diaper 100 disclosed in REFERENCE, the transversely opposite side edges 103, 103 of the front waist region 101, the transversely opposite side edges 104, 104 of the rear waist region 102 and the proximal ends 107, 107 of the respective connector sheet strips 106 are put flat and bonded together wherein the distal ends of the respective connector sheet strips 106, 106 including the engagement members 105, 105 attached thereto extend toward middle of the front waist region 101 as shown in FIG. 5. To put such diaper 100 on the wearer as the diaper of open-type, the connector sheet strips 106 must be turned around from the position in FIG. 5 to the position in FIG. 6 so that the distal ends including the engagement members 105 may extend outward with respect to the rear waist region 102. However, the manner in which the connector sheet strips 106 are bonded as shown in FIG. 5 may cause the connector sheet strips 106 to return to the initial positions after these strips 106 have been turned around. Consequently it may be impossible to maintain these strips 106 extending outward from the front waist region 101 as shown in FIG. 6. Such behavior of the connector sheet strips 106 is troublesome for the mother trying to put the diaper on her baby's body because the mother must, at least temporarily, hold the connector sheet strips 106 so as to extend outward.

SUMMARY OF THE INVENTION

In view of the problem as has been described above, it is an object of the present invention to provide a wearing article including a pair of connector sheet strips extending inward from transversely opposite side edges of the wearing article and serving as fastener means to connect front and rear waist regions improved so that the connector sheet strips can be easily turned around so as to extend outward from the side edges.

According to the present invention, there is provided a disposable wearing article having a back-and-forth direction and a transverse direction orthogonal to the back-and-forth direction, the disposable wearing article comprising a crotch region, a front waist region lying in front of the crotch region and a rear waist region lying behind the crotch region, each of these regions has a pair of side edges opposed to each other in the transverse direction and extending in the back-and-forth direction, the front and rear waist regions having front and rear ends, respectively, opposed to each other in the back-and-forth direction and extending in the transverse direction, and one of the front and rear waist regions being provided on lateral margins extending along the side edges with connector sheet strips adapted to be detachably secured to the other waist region.

Such wearing article further comprises a construction as follows:

Each of the connector sheet strips comprises a proximal end overlapped and bonded together with the lateral margin on an inner surface of the wearing article destined to face a wearer's body of the wearing article and a deformable flap portion extending inward in the transverse direction from the proximal end and provided on the inner surface with fastening means adapted to act upon an outer surface of the other waist region opposed to the inner surface. The proximal end and the lateral margin contain a thermoplastic polymer to ensure that solidification following melting of the thermoplastic polymer integrates the proximal end with the lateral margin in a curved structure wherein the proximal end lies on a convex side and the lateral margin lies on a concave side.

In one preferred embodiment of the present invention, the proximal end and the lateral margin having been integrated with each other present a flexural stiffness in the transverse direction higher than a flexural stiffness presented by an inside region of the wearing article contiguous to the lateral margin.

According to the present invention, the proximal end of the connector sheet strip and the associated lateral margin of the wearing article are integrally bonded together to form the curved structure wherein the proximal end of the connector sheet strip lies on a convex side and the lateral margin lies on a concave side. With such a construction, the flap portion of the connector sheet strip extending inward in the transverse direction of the wearing article can be easily turned around so as to extend outward in the transverse direction of the wearing article.

According to the preferred embodiment of the present invention, the proximal end of the connector sheet strip and the lateral margin are bonded together to form the integrated structure presenting a flexural stiffness in the transverse direction higher than a flexural stiffness presented by the inside region of the wearing article contiguous to the lateral margin. Consequently, the connector sheet strip can be easily turned around without being affected by deformation occurring in this inside region.

DETAILED DESCRIPTION OF THE PREFERRED EMBODIMENTS

Details of a disposable wearing article according to the present invention will be more fully understood from the description of a disposable diaper given hereunder as one embodiment of the disposable wearing article according to the invention.

Figure 1:
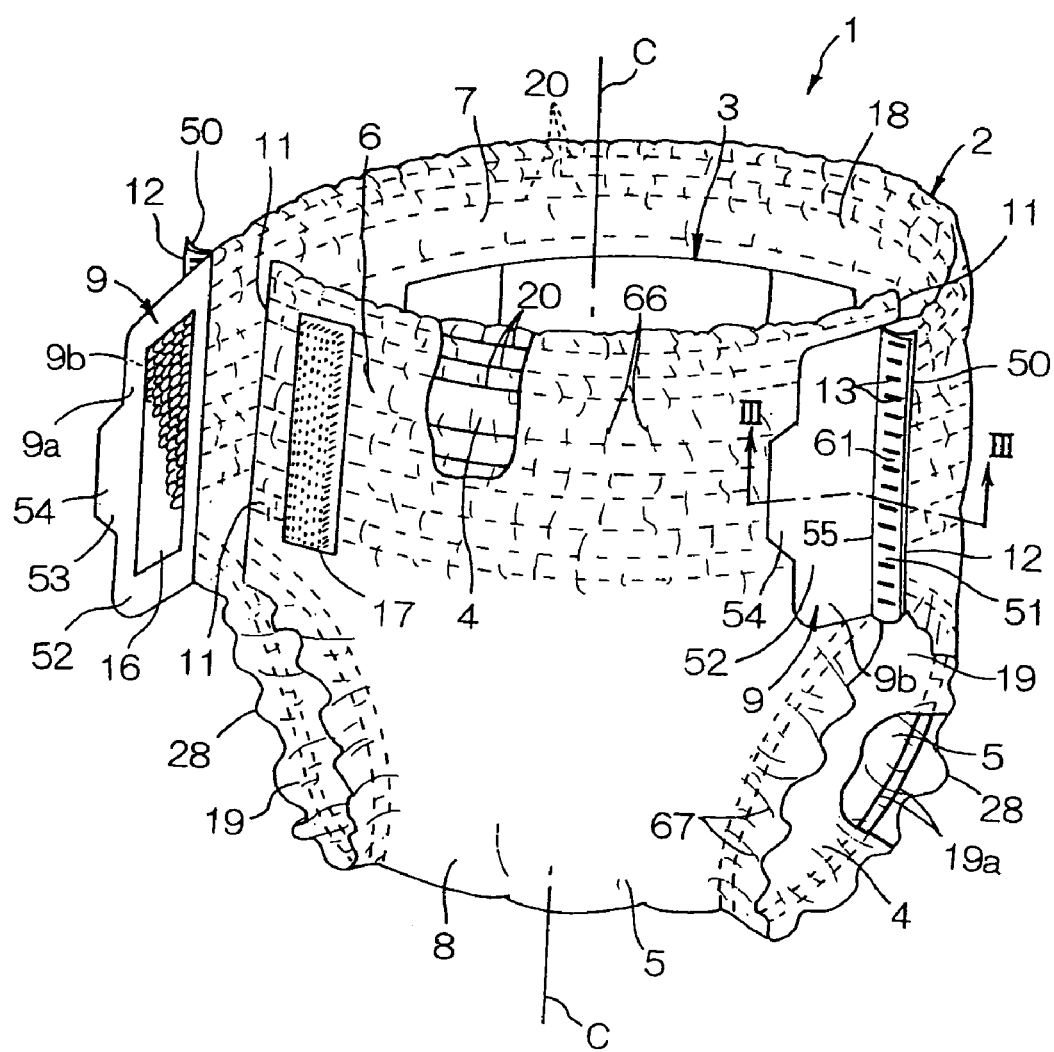
FIG. 1 is a partially cutaway perspective view showing a disposable diaper having front and rear waist regions partially connected to each other.

A disposable diaper 1 shown in FIG. 1 in a partially cutaway perspective view is of a type suitable for baby and comprises a chassis 2 and a bodily fluid absorbent pad 3. The chassis 2 has a crotch region 8, a front waist region 6 extending forward from the crotch region 8 and a rear waist region 7 extending rearward from the crotch region 8. These regions 6, 7, 8 are respectively formed from an outer sheet 5 defined by a first sheet facing the wearer's garment (not shown) and an inner sheet 4 defined by a second sheet lying on the opposite side of the outer sheet 5 and facing the wearer's body. Connector sheet strips 9 defined by a third sheet prepared separately of the inner and outer sheets 4, 5 are put flat together with respective lateral margins 50 extending along transversely opposite side edges 12 of the rear waist region 7 and secured to these lateral margins 50 at a plurality of welding spots 13 thereof arranged intermittently in a vertical direction as viewed in FIG. 1. Each of these connector sheet strips 9 is relatively long in the vertical direction as viewed in FIG. 1 and has inner and outer surfaces 9a, 9b wherein a loop member 16 of a mechanical fastener commonly known under Trademark "MAGIC TAPE" or "VELCRO" is attached to the inner surface 9a by means of a suitable adhesive or welding technique. In the vicinity of each of transversely opposite side edges 11 of the front waist region 6, a hook member 17 of the mechanical fastener is attached to the outer sheet 5 by means of a suitable adhesive or welding technique. With such an arrangement, the front and rear waist regions 6, 7 are detachably connected with each other by means of the connector sheet strips 9 as these loop members 16 and hook members 17 serving as fastening means are engaged together. For convenience of illustration, FIG. 1 shows the front and rear waist regions 6, 7 being in mutually connected state at the right side and in still not mutually connected state at the left side. A waist-hole 18 and a pair of leg-holes 19 are formed as the front and rear waist regions 6, 7 are connected with each other on both sides.

The connector sheet strip 9 has a proximal end 51 secured to the lateral margin 50 of the rear waist region 6 and a deformable flap portion 52 extending toward a longitudinal axis C-C bisecting a width of the front waist region 6. As will be apparent with reference to the right-side connector sheet strip 9 in FIG. 1, the proximal end 51 extends transversely outward with respect to the diaper 1 integrally with the lateral margin 50 and the flap portion 52 extends transversely inward from the proximal end 51. A fold line 55 appears between the proximal end 51 and the flap portion 52 respectively extending in the directions which are opposite to each other. The loop member 16 is attached to the flap portion 52 and a finger-grip 54 is defined by a forward extremity of the flap portion 52 as viewed in a waist-surrounding direction. Of the integrated proximal end 51 and lateral margin 50 describing a curvature, the proximal end 51 lies on a convex side and the lateral margin 50 lies on a concave side.

The diaper 1 further includes a waist elastic members 20 circumferentially extending along the waist-hole 18 and leg-hole elastic members 19a circumferentially extending along the respective leg-holes 19. The chassis 2 is formed with a plurality of gathers 66, 67 each extending orthogonally to the elastic members 20, 19a, respectively, so as to make repetitive undulation along the respective elastic members 20, 19a as these elastic members 20, 19a are left to contract.

Figure 2:
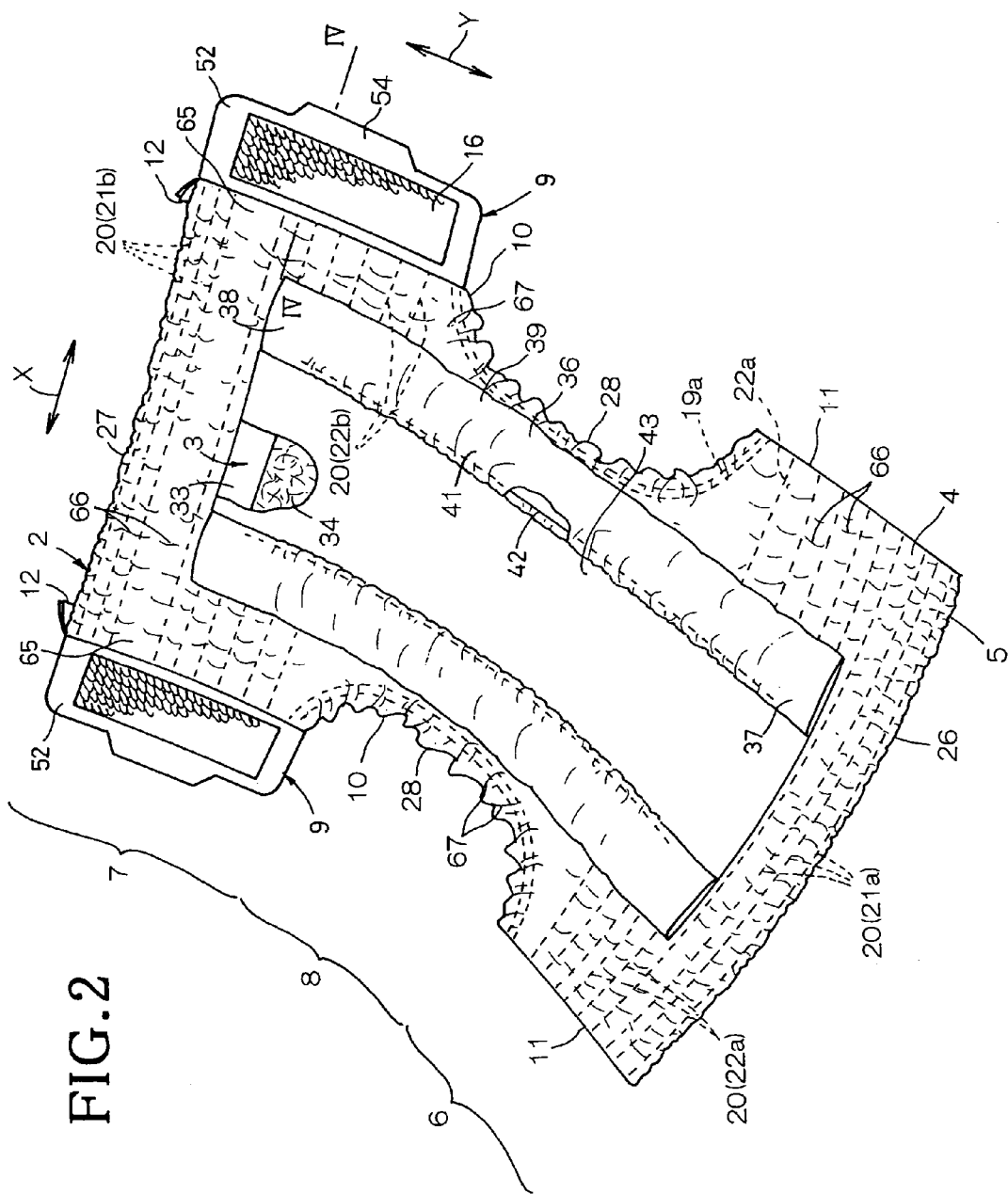
FIG. 2 is a partially cutaway perspective view showing the disposable diaper developed in a transverse direction as well as in a back-and-forth direction.

FIG. 2 is a partially cutaway perspective view showing the diaper 1 of FIG. 1 with the front and rear waist regions 6, 7 disconnected from each other and developed in a transverse direction indicated by a double-headed arrow X as well as in a back-and-forth direction indicated by a double-headed arrow Y insomuch as the gathers 66, 67 do not completely disappear. The transverse direction X corresponds to the waist-surrounding direction of the diaper 1. In the state developed in such manner, the chassis 2 as a whole has a pair of side edges 10 opposed in the transverse direction X and extending in the back-and-forth direction Y. Of these side edges 10, a width between a pair of transversely opposite segments 11 extending in the front waist region 6 is dimensioned to be smaller than a width between another pair of transversely opposite segments 12 extending in the rear waist region 7. A pair of transversely opposite segments 28 of the side edges 10, extending in the crotch region 8 describe circular arcs which are convex inward with respect to the chassis 2. The front and rear waist regions 6, 7 respectively have front and rear ends 26, 27 opposed to each other in the back-and-forth direction Y and extending in the transverse direction X. These front and rear ends 26, 27 cooperate to define a periphery of the waist-hole 18 when the front and rear waist regions 6, 7 are connected with each other as seen in FIG. 1. The waist elastic members 20 provided on the chassis 2 comprise, in addition to at least single first elastic member 21a for the front waist region 6 extending in stretched state along the front end 26 between the opposite side edges 11, 11, and at least single first elastic member 21b for the rear waist region 7 extending in stretched state along the rear end 27 between the opposite side edges 12, 12, a plurality of second elastic members 22a, 22b for the front and rear waist region 6, 7 both lying below the first elastic members 21a, 21b and above the side edges 28 of the crotch region 8 and extending in stretched state between the opposite side edges 11, 11 and between the opposite side edges 12, 12, respectively. The first respective elastic members 21a, 21b are respectively adapted to tighten up the wearer's waist more firmly than the respective second elastic members 22a, 22b respectively can. For this purpose, the elastic members presenting a tensile stress higher than the respective second elastic members 22a, 22b are used as the respective first elastic members 21a, 21b. It is possible without departing from the scope of the invention to eliminate the second elastic member 22a and/or the second elastic member 22b. The chassis 2 is further provided along the side edges 28 of the crotch region 8 with leg elastic members 19a. These waist elastic members 20 and leg elastic members 19a are interposed between the inner sheet 4 and the outer sheet 5 and bonded to at least one of these two sheets 4, 5 preferably intermittently.

As shown in FIG. 2, the bodily fluid absorbent pad 3 comprises a liquid-pervious upper sheet 32, a liquid-impervious lower sheet 33 and a bodily fluid absorbent core 34 sandwiched between these two sheets 32, 33. The upper and lower sheets 32, 33 extend outward beyond a peripheral edge of the core 34 and overlapped and bonded together outside the peripheral edge by means of a adhesive or welding technique. The bodily fluid absorbent pad 3 is provided along transversely opposite side edges thereof with leak barriers 36 preferably made of a liquid-impervious sheet. Each of the leak barriers 36 is bonded along its front and rear ends 37, 38 and outer side edge 39 to the upper sheet 32 but left free along its inner side edge from the upper sheet 32. The inner side edge 41 is provided with an elastic member 42 extending in the back-and-forth direction Y and attached in stretched state thereto. The leak barrier 36 arranged in this manner defines a pocket 43 adapted to receive bodily fluids moving on the upper sheet 32 in the transverse direction X. The body fluid absorbent pad 3 has its lower sheet 33 bonded to the inner sheet 4 of the chassis 2 by means of a hot melt adhesive (not shown).

In the diaper 1 illustrated, both the inner sheet 4 and the outer sheet 5 have a basis weight in a range of about 10 to about 50 g/m² and may be, for example, a nonwoven fabric or film made of a thermoplastic polymer or composite sheet consisting of these nonwoven fabric and film laminated together so far as the thermoplastic polymer is contained therein as an essential ingredient. The upper sheet 32 of the bodily fluid absorbent pad 3 has a basis weight of about 10 to about 30 g/m² may be, for example, a nonwoven fabric or perforated film made of thermoplastic polymer and the lower sheet 33 may be, for example, a film or nonwoven fabric made of a thermoplastic polymer or composite sheet consisting of these film and nonwoven fabric laminated together. The core 34 may be formed by, for example, fluff pulp, or a mixture of fluff pulp and super-absorbent polymer particles compressed to an appropriate thickness and then wrapped with a highly liquid-pervious and liquid-diffusive sheet such as a tissue paper. The connector sheet strip 9 has a basis weight in a range of about 15 to about 200 g/m² and may be, for example, a nonwoven fabric made of a thermoplastic polymer, film made of a thermoplastic polymer or composite sheet consisting of these nonwoven fabric and film laminated together so far as the thermoplastic polymer is contained therein as essential ingredient.

Figure 3:
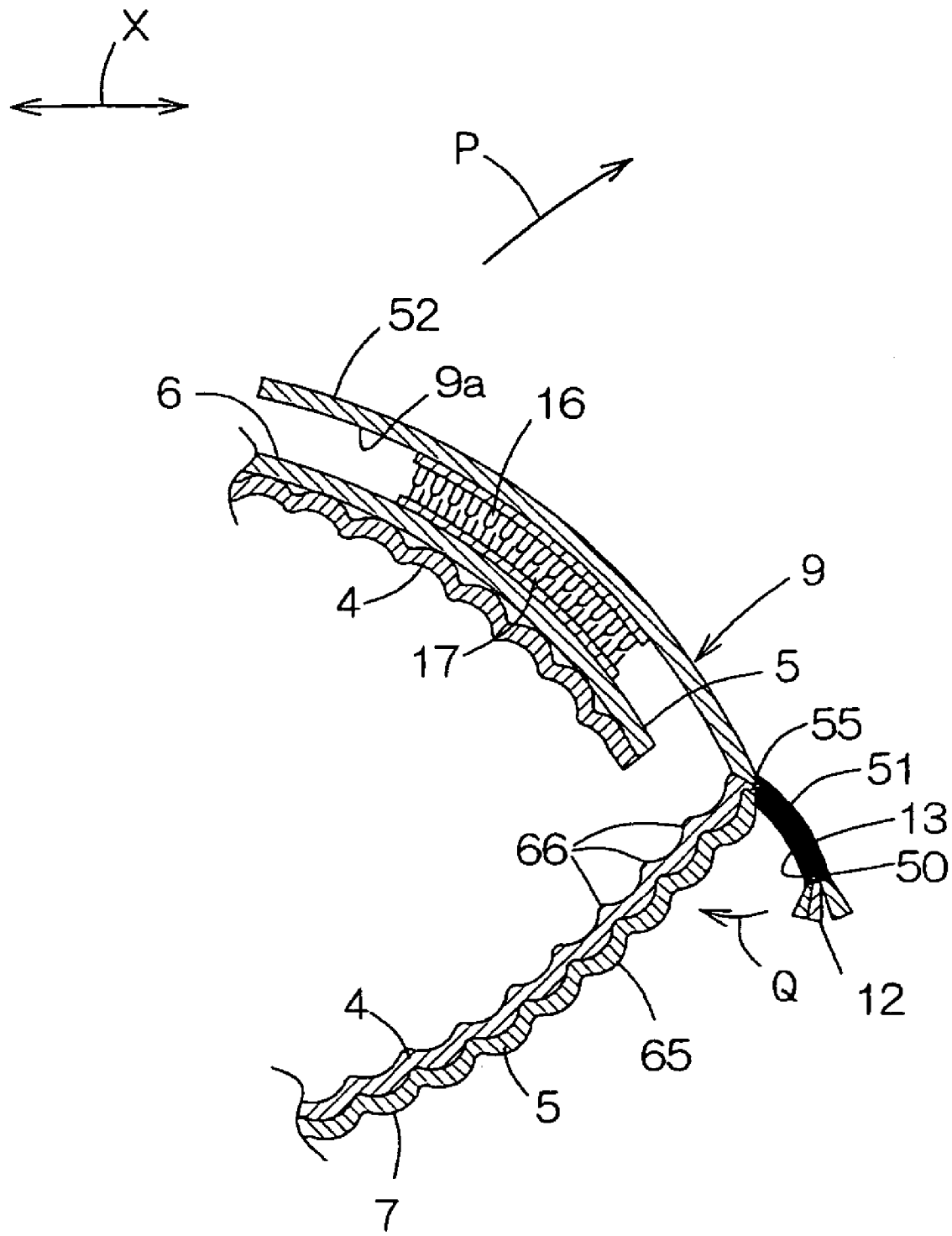
FIG. 3 is a sectional view taken along the line III-III in FIG. 1.

FIG. 3 us a sectional view taken along the line III-III in FIG. 1, wherein the line III-III passes through the welding spots 13. At these welding spots 13, the inner sheet 4, the outer sheet 5 and the connector sheet strip 9 are heated under a pressure so that the thermoplastic polymer contained in these sheets is molten and then these sheets are integrally welded together at the welded spots 13 as the thermoplastic polymer is solidified preferably in film-like state. At these welding spots 13, it is difficult or impossible to distinguish the inner sheet 4, the outer sheet 5 and the connector sheet strip 9 one from another. The lateral margin 50 of the rear waist region 7 including such welding spots 13 describes a curvature so that the proximal end 51 of the connector sheet strip 9 lies on the convex side and the lateral margin 50 of the outer sheet 5 lies on the concave side. Also the non-welded portions 61 between respective pairs of the welding spots 13 successively adjacent in the vertical direction as viewed in FIG. 1 left free from each other follow such curvature. Consequentially, these integrated proximal end 51 and the lateral margin 50 curve downward as viewed in FIG. 1, in other words, toward the rear waist region 7 until the outermost portion of this curve in the transverse direction X is significantly placed aside toward the rear waist region 7 (See FIG. 1). The lateral margin 50 itself comprising the inner and outer sheets 4, 5 overlapped and bonded together is then welded integrally with the connector sheet strip 9 at the welding spots 13 and thereby obtains a flexural stiffness higher that a flexural stiffness of an inside region 65 of the wearing article 1 comprising the inner and outer sheets 4, 5 placed upon each other and is contiguous to the lateral margin 50. As a result, the lateral margin 50 is not readily flexed. With the diaper 1 of such a unique arrangement, the flap portion 52 of the connector sheet strip 9 may be pulled in a direction indicated by an arrow P to invert the loop member 16 and, in response thereto, the lateral margin 50 moves together with the proximal end 51 in a direction indicated by arrow Q. In this way, the connector sheet strip 9 facilitates the flap portion 52 to extend outward in the transverse direction X, as seen in FIG. 2, and in FIG. 4 as will be described later. Such movement of the connector sheet strip 9 can be further facilitated by adjusting a flexural stiffness of the flap portion 52 in the transverse direction X to be higher than a flexural stiffness of the inside region 65 of the wearing article 1 which is contiguous to the lateral margin 50 and merely comprises the inner and outer sheets 4, 5 placed upon each other. In order to ensure the relatively high flexural stiffness of the flap portion 52, a sheet material having the correspondingly high flexural stiffness may be used as the connector sheet strip 9 or, if the connector sheet strip 9 has not a sufficiently high flexural stiffness, the loop member 16 may be attached to the flap portion 52 over substantially its entire inner surface 9a. The fold line 55 appears between the flap portion 52 and the proximal end 51 having a flexural stiffness higher than a flexural stiffness of the flap portion 52.

Figure 4:
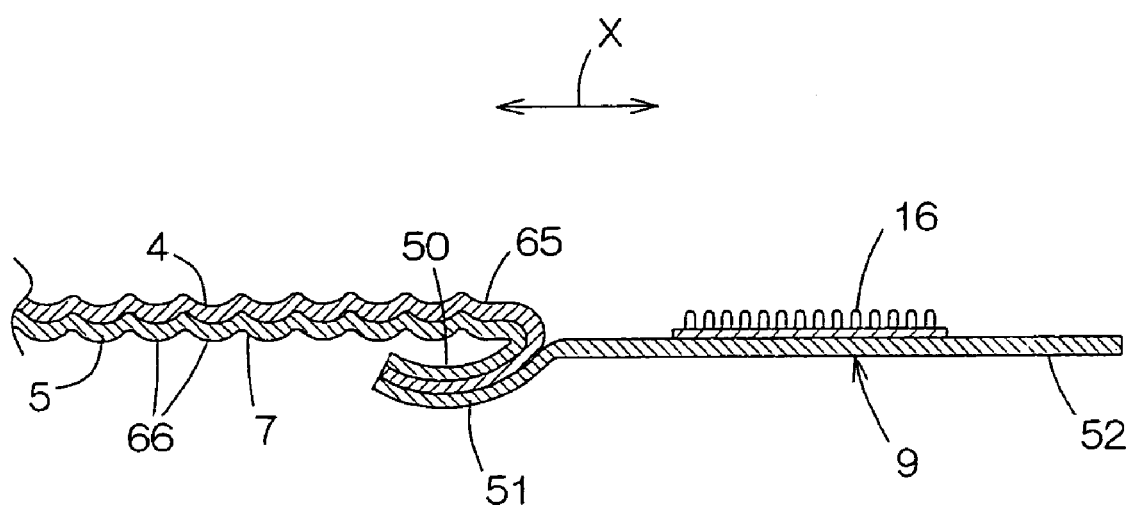
FIG. 4 is a sectional view taken along the line IV-IV in FIG. 2.
Figure 5:
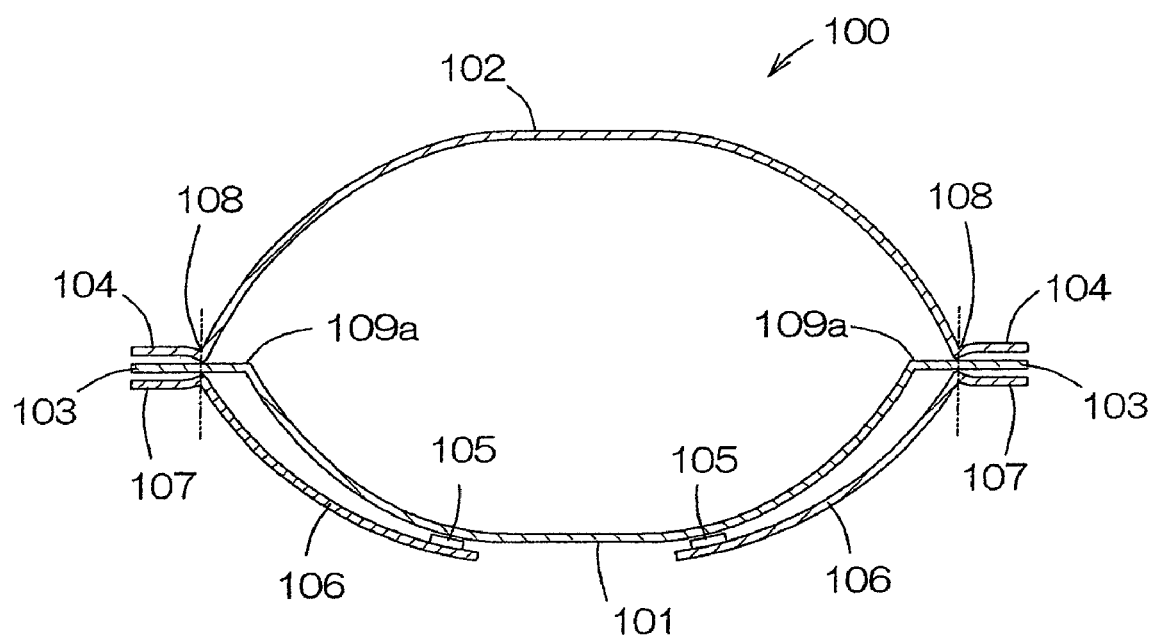
FIG. 5 is a diagram exemplarily illustrating the diaper of prior art.
Figure 6:
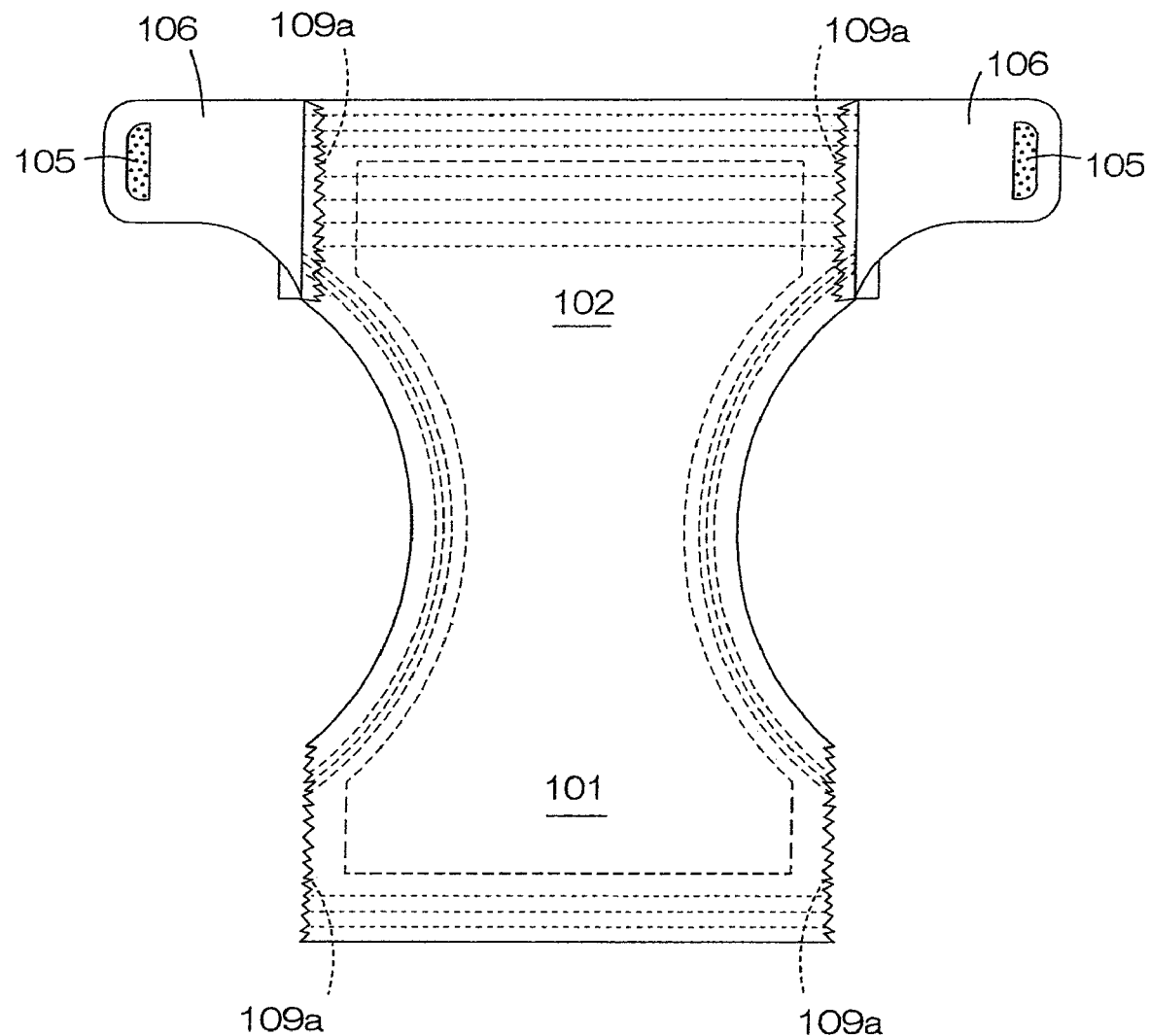
FIG. 6 is a diagram illustrating the diaper of FIG. 5 cut and developed in the transverse direction as well as in the back-and-forth direction.

FIG. 4 is a sectional view taken along the line IV-IV in FIG. 2. The lateral margin 50 of the rear waist region 7 is folded back so as to lie below the rear waist region 7 and the connector sheet strip 9 extends in a horizontal direction. The diaper 1 with the connector sheet strip 9 in the state as shown in FIG. 2 can be smoothly put on the wearer's body since it is not apprehended that the flap portion 52 of the connector sheet strip 9 might unintentionally move toward its closed position.

The gathers 66 formed by the inner and outer sheets 4, of the inside region 65 contiguous to the connector sheet strip 9 enable the connector sheet strip 9 behaving in the manner as has been described in reference with FIGS. 3 and 4 to move quickly in the direction Q to the position shown in FIG. 4. The gathers 66 serving in this manner extend in the vertical direction of the diaper 1 as viewed in FIG. 1.

Without departing from the scope of the invention, it is possible to use the rear waist region 7 having the connector sheet strips 9 attached thereto as the front waist region and to use the front waist region 6 as the rear waist region. It is also possible to reverse the locations of the loop member 16 and the hook member 17 with respect to the case of the illustrated embodiment. Namely, the loop member 16 may be attached to the front waist region 6 and the hook member 17 may be attached to the connector sheet strip 9. Furthermore, the invention may be exploited in a manner that the flap portion 52 of the connector sheet strip 9 is provided on its inner surface 9a with a pressure-sensitive adhesive zone serving as fastening means for the front waist region 6 and the front waist region 6 is provided on its outer sheet 5 with a target zone to which the pressure-sensitive adhesive zone is detachably secured.

While the present invention has been described hereinabove on the basis of the disposable diaper 1, it is possible to exploit the present invention in the other form of wearing articles such as a disposable diaper for adult or incontinent patient, a disposable diaper comprising the bodily fluid absorbent core interposed between the liquid-pervious upper sheet 4 and the liquid-impervious outer sheet 5 rather than the diaper comprising the chassis and the bodily fluid absorbent pad 3, training pants and the diaper cover or urine absorbent pad including not the bodily fluid absorbent pad 3.

The present invention allows the disposable wearing article adapted to be easily put on the wearer's body to be produced.

The entire discloses of Japanese Patent Application Nos. 2004-301262 filed on Oct. 15, 2004 including specification, drawings and abstract are herein incorporated by reference in its entirety.

What is claimed is:

1. A disposable wearing article having a back-and-forth direction and a transverse direction orthogonal to said back-and-forth direction, said disposable wearing article comprising:
   as viewed in said back-and-forth direction, a crotch region, a front waist region lying in front of said crotch region and a rear waist region lying behind said crotch region, wherein each of said regions has a pair of side edges opposed to each other in said transverse direction and extending in said back-and-forth direction, said front and rear waist regions further having front and rear ends, respectively, opposed to each other in said back-and-forth direction and extending in said transverse direction, and one of said front and rear waist regions being provided on lateral margins extending along said side edges with connector sheet strips adapted to be detachably secured to the other waist region; and
   each of said connector sheet strips comprising (i) a proximal end overlapped and bonded together with one of said lateral margins on an inner surface of said wearing article adapted to face a wearer's body in use, and (ii) a deformable flap portion extending inward in said transverse direction from said proximal end and provided on a side facing the inner surface of said wearing article with a fastening element detachably engageable with an outer surface of said wearing article in the other waist region, said outer surface being adapted to face away from the wearer's body in use;
   wherein the proximal end of each of said connector sheet strips and the corresponding lateral margin contain a thermoplastic polymer and are bonded together at welding spots which comprise said thermoplastic polymer in a molten and then solidified state, the thermoplastic polymer in the molten and then solidified state defining a curved structure which has opposite exposed surfaces, wherein one of said exposed surfaces is concave and the other is convex, and wherein said proximal end lies on the side of the convex, exposed surface and the corresponding lateral margin lies on the side of the concave, exposed surface.

2. The disposable wearing article defined by claim 1, wherein said proximal end of each of said connector sheet strips and the corresponding lateral margin integrated with each other at said welding spots present a flexural stiffness in said transverse direction higher than a flexural stiffness presented by an inside region of the wearing article contiguous to said lateral margin.

3. The disposable wearing article defined by claim 2, wherein the flap portion of each of said connector sheet strips presents a flexural stiffness in said transverse direction higher than the flexural stiffness presented by the inside region of the wearing article contiguous to the lateral margin bonded to the proximal end of said connector sheet strip.

4. The disposable wearing article defined by claim 3, wherein
   said proximal end of each of said connector sheet strips and the corresponding lateral margin integrated with each other at said welding spots present the flexural stiffness in said transverse direction higher than the flexural stiffness presented by the flap portion of said connector sheet strip.

5. The disposable wearing article defined by claim 1, wherein the fastening element of each of said connector sheet strips is located outside and is not defined by the curved structure in which the proximal end of said connector sheet strip is bonded to the corresponding lateral margin.

6. The disposable wearing article defined by claim 1, wherein
   the flap portion of each of said connector sheet strips is moveable between a first position where said flap portion extends in the transverse direction inward from the respective proximal end and a second position where said flap portion extends in the transverse direction outward from said proximal end.

7. The disposable wearing article defined by claim 6, wherein
   each of said connector sheet strips further comprises a folding line located between the proximal end and the flap portion of said connector sheet strip; and
   the curved structure in which the proximal end of each of said connector sheet strips is bonded to the corresponding lateral margin facilitates pivotal movement of the flap portion of said connector sheet strip from the first position to the second position about the respective folding line.

8. The disposable wearing article defined by claim 7, wherein, in each of said connector sheet strips, the fastening element and the curved structure are completely located on opposite sides of said folding line.

9. The disposable wearing article defined by claim 1, wherein
   said connector sheet strips have regions located outside the welding spots and containing the thermoplastic polymer which is not in the molten and then solidified state.

10. The disposable wearing article defined by claim 1, further comprising
    a topsheet defining the inner surface of said article; and
    a backsheet defining the outer surface of said article;
    wherein said welding spots comprise materials of the topsheet, the backsheet and the connector sheet strips in the molten and then solidified state.

11. A disposable wearing article having a longitudinal direction and a transverse direction orthogonal to each other, said article comprising:
    a first waist region;
    a second waist region;
    a crotch region extending in the longitudinal direction between the first and second waist regions;
    each of said regions having a pair of side edges opposed to each other in said transverse direction, and opposite inner and outer surfaces, the inner surface being adapted to face a wearer's body in use and the outer surface being adapted to face away from the wearer's body in use; and connector sheet strips attached to said first waist region in vicinities of the side edges of said first waist region, respectively;

wherein each of said connector sheet strips respectively comprises:

a proximal end fixed, at a plurality of welding spots, to the inner surface of said first waist region in the vicinity of one of said side edges of said first waist region;

a deformable flap portion moveable between a first position where said flap portion extends in the transverse direction inward from said proximal end and a second position where said flap portion extends in the transverse direction outward from said proximal end, said flap portion having a surface that is opposed to said inner surface of said first waist region when the flap portion is in the first position;

a fastening element provided on said surface of said flap portion and releasably engageable with the outer surface of the second waist region; and a folding line between said flap portion and said proximal end, said folding line extending along said proximal end to facilitate pivotal movement of said flap portion from the first position to the second position;

wherein the welding spots comprise a thermoplastic polymer in a molten and then solidified state, the thermoplastic polymer in the molten and then solidified state defining a curved structure which has opposite exposed surfaces, wherein one of said exposed surfaces is concave and the other is convex, and wherein said proximal end lies on the side of the convex, exposed surface and the corresponding lateral margin lies on the side of the concave, exposed surface.

12. The disposable wearing article defined by claim 11, wherein said first waist region has zones immediately adjacent the welding spots where the proximal ends of the connector sheet strips are bonded to the respective side edges of said first waist region, said zones being located inboard of the adjacent welding spots and formed with gathers; and a flexural rigidity of each said proximal end bonded with the respective side edge of the first waist region, as measured in said transverse direction, is higher than that of said first waist region in said zones.

13. The disposable wearing article defined by claim 12, wherein the flap portion of each of said connector sheet strips presents a flexural stiffness in said transverse direction higher than the flexural stiffness presented by said zones of said first waist region.

14. The disposable wearing article defined by claim 13, wherein the flexural rigidity of each said proximal end bonded with the respective side edge of the first waist region is higher than the flexural stiffness presented by the flap portion of the respective connector sheet strip.

15. The disposable wearing article defined by claim 11, wherein, in each of said connector sheet strips, the fastening element and the curved structure are completely located on opposite sides of said folding line.

16. The disposable wearing article defined by claim 15, wherein said connector sheet strips and the first waist region have areas located outside the welding spots and containing the thermoplastic polymer which is not in the molten and then solidified state.

17. The disposable wearing article defined by claim 16, further comprising a topsheet containing the thermoplastic polymer and defining the inner surface of said first waist region; and a backsheet containing the thermoplastic polymer and defining the outer surface of said first waist region;

wherein said welding spots comprise the thermoplastic polymer of the topsheet, the backsheet and the connector sheet strips in the molten and then solidified state.

* * * * *